United States Patent [19]
McMichael

[11] Patent Number: 6,020,314
[45] Date of Patent: Feb. 1, 2000

[54] METHODS FOR TREATMENT OF NEUROLOGICAL DISORDERS

[75] Inventor: John McMichael, Delanson, N.Y.

[73] Assignee: Milkhaus Laboratory, Inc., Delanson, N.Y.

[21] Appl. No.: 09/132,352

[22] Filed: Aug. 11, 1998

[51] Int. Cl.[7] .............................. A61K 38/00; C07K 5/00; C07K 7/00

[52] U.S. Cl. .............................. 514/21; 514/12; 530/324; 530/300

[58] Field of Search ................ 514/12, 21; 530/300–324

[56] References Cited

FOREIGN PATENT DOCUMENTS

| 9852593 | 11/1998 | WIPO | ............................. A61K 38/00 |
| WO 98/52593 | 11/1998 | WIPO | ............................. A61K 38/00 |

*Primary Examiner*—Avis M. Davenport
*Attorney, Agent, or Firm*—Marshall, O'Toole, Gerstein, Murray & Borun

[57] ABSTRACT

Methods are provided of treating the symptoms of neurological disorders including those selected from the group consisting of autism, multiple sclerosis and enuresis by administering to a patient diagnosed with the neurological disorder a composition containing an effective amount of secretin.

6 Claims, No Drawings

METHODS FOR TREATMENT OF NEUROLOGICAL DISORDERS

BACKGROUND OF THE INVENTION

The present invention relates to methods of treatment of neurological disorders, including those neurological disorders selected from the group consisting of autism, multiple sclerosis, and enuresis (bed-wetting).

Autism is a syndrome of early childhood which is characterized by abnormal social relationships, language disorder, rituals and compulsive phenomena including an insistence on the preservation of sameness and uneven intellectual development. The syndrome appears to be affected by genetic factors and predominantly affects boys. Causes of the disorder are unclear although individual cases have been associated with the congenital rubella syndrome, cytomegalic inclusion disease, phenylketonuria and the fragile X syndrome.

Treatment of autism has generally been limited to systematic application of behavior and speech therapy. While therapy with butyrophenones has provided some benefits in limiting the most severe forms of behavior such therapy has not been found to resolve the psychosis. Moreover, research with serotonergic antagonists such as fenflurimine to treat unmanageable behavior remains controversial. Accordingly, there remains a need in the art for new treatments for autism.

Multiple sclerosis is a slowly progressing demyelinating disease of the central nervous system which is insidious and characterized by multiple and varied neurological symptoms characterized by remissions and exacerbations. The disease is believed to be immunological in nature but treatment with immuno-suppressive agents is not advised. Instead, treatment with oral prednisone and with dexamethasone has been common with recent treatment with interferon beta showing potentially promising results. Nevertheless, there remains a desire in the art for new and improved methods for treatment of the symptoms of multiple sclerosis.

Enuresis (bed-wetting) is the involuntary and repeated passage of urine while asleep occurring at an age when voluntary control is generally expected. Enuresis is familial and tends to occur more often in boys than in girls. Traditional treatments have included bladder exercises, motivational counseling, and treatment with imipramine. More recently, treatment with enuresis alarms has been preferred but is reported to have only a 70% effectiveness rate among 5 to 15-year olds with a relapse rate of 10 to 15%. Accordingly, there still remains a desire for effective means for treatment of enuresis.

Of interest to the present application is secretin which is a polypeptide hormone having 27 amino acid residues which is secreted by endocrine cells of the small intestine. Secretion of the hormone is stimulated by low pH as occurs with dumping of the food bolus from the stomach to the intestine. This low pH stimulates secretin to induce the secretion of pancreatic juice that has a high sodium bicarbonate concentrations which thus neutralized the HCl of the stomach contents. Secretin is used in diagnostic methods to determine gastric activity and small intestine function but its use has not been taught for therapeutic purposes.

SUMMARY OF THE INVENTION

The present invention is directed to methods for the treatment of neurological disorders and their symptoms. In particular, the invention is directed toward the treatment of neurological disorders and associated symptoms which disorders are selected from the group consisting of autism, multiple sclerosis, and enuresis. Specifically, the invention provides a method of treating the symptoms of neurological disorders comprising the step of administering to a patient diagnosed with a neurological disorder a composition comprising an effective amount of secretin. The methods of the invention preferably administer secretin at a daily dosage of from about $10^{-8}$ to $10^{-3}$ mg and more preferably at a daily dosage of about $10^{-4}$ to $10^{-4}$ mg. According to the invention the secretin is preferably administered in the presence of a pharmaceutically acceptable diluent. The compositions of the invention may be administered by a variety of routes of administration including intravenous, intramuscular, subcutaneous, intrathecal, topical, inhalation and oral, with subcutaneous and sublingual administration being preferred. When administered sublingually, a preferred composition comprises $4\times10^{-6}$ mg secretin per 0.05 ml drop. The composition is then preferably applied sublingually from once to four times daily.

DETAILED DESCRIPTION OF THE INVENTION

The present invention provides method for the treatment of neurological disorders (and symptoms thereof) selected from the group consisting of autism, multiple sclerosis and enuresis through the administration of effective amounts of secretin. The invention also provides pharmaceutical compositions comprising an effective amount of secretin in combination with a physiologically acceptable carrier for administration to patients.

Provided below are case histories of patients being treated according to the invention which provide evidence of the effectiveness of the treatment methods described herein. The following Examples are intended to illustrate practice of the preferred embodiments of the invention. Numerous additional embodiments and improvements are apparent upon consideration of the following Examples.

EXAMPLE 1

According to this example, an eight year old boy with autism who exhibited symptoms of bed wetting, poor verbalization and poor sleep patterns was treated with one sublingual drop of secretin daily ($4\times10^{-6}$ ml secretin per 0.05 ml drop). After one day of treatment the subject exhibited elimination of bed wetting, increased verbalization, increased cognition, and was sleeping well. Later, when administration of secretin was terminated wet wetting reoccurred. When secretin administration was resumed bed wetting was again eliminated. The other symptoms exhibited similar behavior where they worsened upon removal of secretin administration but improved upon resumption of secretin therapy.

EXAMPLE 2

According to this example, a five year old autistic boy was treated according to the method of Example 1 with one drop of secretin ($4\times10^{-6}$ ml secretin per 0.05 ml drop) daily. After about three days of treatment according to the invention, the patient showed cognitive and motor improvement, could follow a pointing finger and exhibited an improved sleep pattern. The subject also showed an increased spectrum of desired and tolerated foods, cried with tears for the first time ever, began to use three word sentences, and began to self-correct verbal errors.

EXAMPLE 3

According to this example, a seven year old autistic boy was treated according to the method of Example 1 with one drop of secretin ($4\times10^{-6}$ ml secretin per 0.05 ml drop) daily. With the first week of treatment the subject exhibited improved attitude, better manners, improved playing and appropriate self-entertainment. The subject also exhibited improved tolerance to noise and confusion, improved eye contact, and improved signing and verbal communication.

EXAMPLE 4

According to this example, an 8 year old female with a history of emotional and behavioral problems and diagnosed with attention deficit disorder (ADD)/attention deficit hyperactivity (ADH) was treated with secretin at the rate of one drop ($4\times10^{-6}$ ml secretin per 0.05 ml drop) daily. Within two days she reported, and her mother confirmed, better behavior, decreased irritability and decreased or eliminated "explosiveness." After three weeks of the improved status, the patient discontinued the drops. Within 48 hours after ending secretin therapy, the patient was more explosive, more irritable and depressed. Resumption of administration of secretin restored the improved condition.

EXAMPLE 5

According to this example, a 48 year old male with multiple sclerosis was treated by sublingual administration of one drop of secretin ($4\times10^{-6}$ ml secretin per 0.05 ml drop) from once to three times daily. The subject reported improved nocturia (having to get up once per night vs. 4 times per night previously), decreased bladder urgency during waking hours, improved mobility, more regular bowel function, complete elimination of muscle spasms that previously had interfered with sleep and mobility, improved appetite.

EXAMPLE 6

According to this example, a five year old male diagnosed with primary enuresis and having a family history of the same was treated by administration of one drop of secretin ($4\times10^{-6}$ ml secretin per 0.05 ml drop) twice daily. After one month of treatment the subject did not wet his bed once.

EXAMPLE 7

According to this example, a ten year old female diagnosed with primary enuresis was treated by administration of one drop of secretin ($4\times10^{-6}$ ml secretin per 0.05 ml drop) twice daily. Treatment resulted in no bed-wetting for two full months. Treatment was then discontinued and bed-wetting reoccurred. After resuming treatment no more bed-wetting occurred.

EXAMPLE 8

According to this example, an eleven year old male diagnosed with primary enuresis had previously been treated with a bed-wetting alarm and other procedures which had been unsuccessful. The subject was treated by administration of one drop of secretin ($4\times10^{-6}$ ml secretin per 0.05 ml drop) twice daily. Treatment initially resulted in dryness 50% of the time. When treatment was increased to two drops of secretin twice daily, wetting decreased to 10 to 15%.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of treating the symptoms of neurological disorders selected from the group consisting of autism, multiple sclerosis and enuresis comprising the step of administering to a patient diagnosed with said neurological disorder a composition comprising an effective amount of secretin wherein the secretin is administered at a daily dosage of about $10^{-6}$ to $10^{-4}$ mg.

2. The method of claim 1 wherein the secretin is administered by means selected from the group consisting of intravenous, intramuscular, subcutaneous, intrathecal, and sublingual.

3. The method of claim 1 wherein the neurological disorder is autism.

4. The method of claim 1 wherein the neurological disorder is multiple sclerosis.

5. The method of claim 1 wherein the neurological disorder is enuresis.

6. A pharmaceutical composition in dosage form for administration to a subject comprising an effective amount of secretin for treatment of a neurological disorder selected from the group consisting of autism, multiple sclerosis and enuresis in combination with a physiologically acceptable carrier wherein the secretin is present at a daily dosage of about $10^{-6}$ to $10^{-4}$ mg.

* * * * *